(12) United States Patent
Popelar et al.

(10) Patent No.: US 9,109,135 B2
(45) Date of Patent: Aug. 18, 2015

(54) COMPOSITION FOR COATING OF A SURFACE, AND A COATING

(71) Applicant: SinterCast AB, Stockholm (SE)

(72) Inventors: Patrik Popelar, Katrineholm (SE); Tobias Björklind, Gnesta (SE)

(73) Assignee: SinterCast AB, Stockholm (SE)

( * ) Notice: Subject to any disclaimer, the term of this patent is extended or adjusted under 35 U.S.C. 154(b) by 0 days.

(21) Appl. No.: 14/329,476

(22) Filed: Jul. 11, 2014

(65) Prior Publication Data

US 2015/0013477 A1    Jan. 15, 2015

(30) Foreign Application Priority Data

Jul. 12, 2013  (SE) ...................................... 1350875

(51) Int. Cl.
| | | |
|---|---|---|
| *C09D 1/02* | (2006.01) | |
| *C09D 133/00* | (2006.01) | |
| *C04B 28/26* | (2006.01) | |
| *B05D 1/28* | (2006.01) | |
| *B05D 3/04* | (2006.01) | |
| *B05D 5/00* | (2006.01) | |
| *C08K 3/22* | (2006.01) | |
| *C08K 3/30* | (2006.01) | |
| *C08K 3/34* | (2006.01) | |
| *C08K 3/38* | (2006.01) | |
| *C08K 5/05* | (2006.01) | |
| *C09D 7/12* | (2006.01) | |
| *G01N 1/12* | (2006.01) | |
| *C04B 111/00* | (2006.01) | |

(52) U.S. Cl.
CPC .............. *C09D 133/00* (2013.01); *B05D 1/28* (2013.01); *B05D 3/0406* (2013.01); *B05D 5/00* (2013.01); *C04B 28/26* (2013.01); *C08K 3/22* (2013.01); *C08K 3/30* (2013.01); *C08K 3/34* (2013.01); *C08K 3/38* (2013.01); *C08K 5/05* (2013.01); *C09D 7/1216* (2013.01); *G01N 1/125* (2013.01); *C04B 2111/00525* (2013.01); *C04B 2111/00939* (2013.01); *C08K 2003/3009* (2013.01); *C08K 2003/385* (2013.01)

(58) Field of Classification Search
CPC ...... C09D 1/02; C09D 133/00; C09D 7/1216; C08K 3/38; C08K 3/34; C04B 28/26; C04B 22/14
USPC .......................................... 106/627; 428/457
See application file for complete search history.

(56) References Cited

U.S. PATENT DOCUMENTS

| | | | |
|---|---|---|---|
| 3,351,123 | A | 11/1967 | Payne et al. |
| 6,571,856 | B1 | 6/2003 | Popelar et al. |

FOREIGN PATENT DOCUMENTS

| | | | |
|---|---|---|---|
| EP | 1034419 | A1 | 9/2000 |
| JP | 6-142896 | A | 5/1994 |
| JP | 6-504322 | A | 5/1994 |
| JP | 7-113771 | A | 5/1995 |
| JP | 10-512957 | A | 12/1998 |
| JP | 11-304736 | A | 11/1999 |
| JP | 2001-269767 | A | 10/2001 |
| JP | 2002-533657 | A | 10/2002 |
| JP | 2010-131665 | A | 6/2010 |
| WO | 86/01755 | A1 | 3/1986 |
| WO | 92/06809 | A1 | 4/1992 |
| WO | 96/23206 | A1 | 8/1996 |
| WO | 97/35184 | A1 | 9/1997 |
| WO | 99/28726 | A1 | 6/1999 |
| WO | 00/37698 | A1 | 6/2000 |

OTHER PUBLICATIONS

Office Action received for Swedish Patent Application No. 1350875-9, mailed on Jan. 16, 2014, 7 pages.
Intention to Grant received for Swedish Patent Application No. 1350875-9, mailed on Jun. 11, 2014, 61 pages.
Office Action received for Japanese Patent Application No. 2014-132418, mailed on Sep. 22, 2014, 8 pages (4 pages of English Translation and 4 pages of official copy).
Extended European Search Report received for European Patent Application No. 14173607.4, mailed on Feb. 2, 2015, 7 pages.
"Marktübersicht Schlichtesysteme", Giesserei Erfahrungsaustausch, Aug. 7, 2012, 7 pages.

*Primary Examiner* — Pegah Parvini
(74) *Attorney, Agent, or Firm* — Morrison & Foerster LLP (57) ABSTRACT

A composition for coating of a surface intended to be exposed to a metal melt consists of 8-18 wt-% of a refractory component, 50-75 wt-% of solvent, preferably water, 10-20 wt-% of an inorganic binder, 0-10 wt-%, preferably 2-10 wt-%, of an organic binder, 0.3-7 wt-%, preferably 2-6 wt-%, more preferably, 3-5 wt-% of pyrite; and optionally up to 10 wt-%, preferably up to 5 wt-%, of additional additive or additives. The composition results in a coating on a surface, which coating is able to reduce the dissolved elemental magnesium content in a metal melt to which the surface is exposed.

28 Claims, 3 Drawing Sheets

COMPOSITION FOR COATING OF A SURFACE, AND A COATING

REFERENCE TO RELATED APPLICATIONS

This application claims priority from Swedish Patent Application No. 1350875-9, filed on Jul. 12, 2013, the content of which is incorporated herein by reference in its entirety.

FIELD OF THE INVENTION

The present invention relates to a composition for coating of a surface intended to be exposed to a metal melt, such as a surface of components used in the production of metal melts, particularly in the production of cast iron, compacted graphite iron or ductile iron. The present invention also relates to a coating obtainable by means of coating a substrate with the composition. Furthermore, the present invention relates to a sampling device for thermal analysis of solidifying metal melts and a process for manufacturing such a sampling device.

BACKGROUND OF THE INVENTION

Coatings may be used for example for providing a protective coating for a base metal, usually a ferrous metal, of ladles used for molten metal melts, such as aluminium, magnesium or zinc based melts. In order to be effective, the coating must be fairly abrasion resistant, be sufficiently thick and adequately adherent to the surface of the base metal. It is also possible to use coatings for achieving other functional purposes, such as when using reactive coatings.

Thermal analysis is a technique monitoring variations in temperature change of certain molten substances during solidification to be able to determine the microstructure and hence properties of the substances in solid form. This is accomplished by taking a sample from the melt, transferring it into a sample vessel and recording and evaluating a time-dependent temperature change in the sample during solidification, by means of temperature responsive means, such as thermocouples or other devices known in the art.

WO 86/01755 discloses a method for producing compacted graphite cast iron by using thermal analysis. A sample is taken from a bath of molten cast iron and this sample is permitted to solidify during 0.5 to 10 minutes. The temperature is recorded simultaneously by two temperature responsive means, one of which is arranged in the centre of the sample and the other in the immediate vicinity of the vessel wall. So-called cooling curves representing the temperature of the iron sample as a function of time are recorded for each of the two temperature responsive means. According to this document it is then possible to determine the necessary amount of structure-modifying agents that must be added to the melt in order to obtain the desired microstructure.

Moreover, WO 92/06809 discloses a method for production of compacted graphite iron using thermal analysis. A melt of a suitable composition and structure is prepared and a modifying agent, such as magnesium, is added to the melt in an amount which is expected to be sufficient to produce compacted graphite iron. A sample is then extracted from the melt in a sample vessel, the wall of which is coated on its inside surface with a layer consisting of a material which will react with dissolved elementary magnesium present in the vicinity of said wall. Two thermocouples, one placed in the centre of the melt and the other in the vicinity of the vessel wall, are used to record the temperatures as a function of time during solidification of the sample melt, thereby giving information of phase transformations during solidification. The recorded temperature curves are thus used to determine if the magnesium content and the inoculation of the melt, from which the sample has been taken, has to be modified in order to achieve the desired phase transformations of the melt when producing a casting thereof in order to achieve the desired structure of graphite in the casting.

The fact that the vessel wall is coated with a layer consisting of a material which will react with dissolved elementary magnesium, and the arrangement of the thermocouples in the sample, gives two separate temperature readings giving information regarding the magnesium content of the melt. The thermocouple in the vicinity of the vessel wall records a temperature curve of a melt with a predetermined lower level of dissolved elementary magnesium (determined by the selected coating) than the thermocouple arranged in the centre of the sample melt and thus the structural changes of said composition. Thus, by comparing the readings of the two thermocouples, a more accurate measurement of the magnesium content of sample melt and thus the solidification properties of the melt from which the sample has been taken, is achieved.

The use of a coating which reduces the content of magnesium in the vicinity of the vessel wall of a sampling device may also advantageously be used when conducting thermal analysis of other metal melts, such as ductile cast iron (comprising nodular graphite particles) or grey iron (comprising flake/lamellar graphite particles).

WO 97/35184 discloses a sampling vessel where a part of the inner surface is coated with a reactive layer, the layer being of a substance which will lower the concentration of dissolved elementary magnesium to increase the accuracy of the solidification structure predictions of molten cast iron. According to this document, one temperature responsive means is placed in the centre of the sample vessel, another temperature responsive means is placed close to the inner surface of the sample vessel which has been coated with the reactive layer and a third temperature responsive means close to the inner surface of the sample vessel which has not been coated with the reactive layer. Each of the temperature responsive means are used to record the temperature of the melt during the solidification process as a function of time to obtain temperatures which are to be evaluated to determine the evolution of the solidification process. The reactive coating comprises 0-5 sulphur, 0-10% oxides of silicon, manganese or iron, and/or 0-0.5% oxides of potassium and sodium.

It has now been found that the previously known coatings for sampling devices intended to be used for thermal analysis does not always work as intended and may be difficult to give sufficiently accurate readings during thermal analysis, especially in the case of thermal analysis of ductile iron. Thus, there is still room for further improvements of previously known coatings.

SUMMARY OF THE INVENTION

The object of the invention is a composition for coating of a surface intended to be exposed to a metal melt, which will result in a coating sufficiently adherent to the surface, sufficiently stable at high temperatures and which will enable a reduction of the elemental magnesium content of a metal melt in contact with the coated surface.

The object is achieved by a composition in accordance with independent claim 1, a coating in accordance with independent claim 9 and a process for coating according to claim 18. Embodiments are defined by the dependent claims.

The present invention also relates to a sampling device for thermal analysis of solidifying melt in accordance with claim 19 and a process for manufacturing a sampling device for thermal analysis of solidifying melt in accordance with claim 20.

The composition for coating of a surface intended to be exposed to a metal melt essentially consists of:
- 8-18 wt-% of a refractory component;
- 50-75 wt-% of solvent, preferably water;
- 10-20 wt-% of an inorganic binder;
- 0-10 wt-%, preferably 2-10 wt-%, of an organic binder;
- 0.3-7 wt-%, preferably 2-6 wt-%, more preferably, 3-5 wt-% of pyrite;
- optionally up to 10 wt-% in total, preferably up to 5 wt-% in total, of one or more additional additives; and unavoidable impurities.

The refractory component is preferably selected from the group consisting of boron nitride, zirconia, alumina and mixtures thereof. Preferably, the refractory component is boron nitride.

The inorganic binder may suitably be a silicate, such as sodium silicate or potassium silicate. The organic binder may suitably be acrylic. The composition may also comprise one or more additional additives, such as additives selected from the group consisting of surfactants, viscosity modifiers, additives for flowability, additives for high temperature stability, additives for improved adhesiveness to a substrate, or mixtures thereof.

The pyrite is preferably in the form of a granular powder. Moreover, the average particle size of the pyrite is preferably 40-70 µm.

The composition as described above is used to coat a surface intended to contact a metal melt. The coating may be performed by any suitable conventional coating technique known in the art, such as brushing, painting or dipping of a substrate. The composition is then subjected to a drying or evaporation step to essentially remove the solvent.

The composition adheres well to various types of substrates, such as metal surfaces and ceramic surfaces, and is easy to apply thereto by conventional techniques. It is also highly temperature resistant while still providing a sufficiently reactive coating. The fact that sulphur is present in the form of pyrite ensures that the sulphur is sufficiently available for reaction with dissolved elementary magnesium in the metal melt in contact with a coating obtained by means of the composition.

The coating according to the invention, which is obtainable by means of the above given composition, essentially consists of:
- 26-60 wt-% of a refractory component;
- 33-67 wt-% of an inorganic binder;
- 0-3.5 wt-%, preferably 1.5-3.5 wt-%, of an organic binder;
- 1-23 wt-%, preferably 6.5-20 wt-%, more preferably 10-16.5 wt-%, of pyrite;
- optionally up to 10 wt-%, preferably up to 5 wt-%, of residual solvent;
- optionally up to 33 wt-% in total, preferably up to 16 wt-% in total, of one or more additional additives; and unavoidable impurities.

The sampling device for thermal analysis of solidifying metal according to the invention comprises a container adapted to comprise a sample quantity of a metal melt during thermal analysis and temperature responsive means adapted to extend into the sample quantity during thermal analysis. The container comprises an inner surface adapted to face a sample quantity of the melt during thermal analysis, and an outer surface adapted to face the ambient atmosphere during thermal analysis. At least a part of the inner surface, preferably the whole inner surface, of the container comprises the coating according to the invention. The container is preferably a doubled-wall container.

Examples of designs of the sampling device may for example be sampling devices as disclosed in EP 1 034 419, WO 96/23206 or WO 97/35184, hereby incorporated by reference. The composition may be applied to the inner surface of any of the containers disclosed in these documents.

The sampling device simulates a spherical solidification of the molten metal inside the container, which is the most reliable and accurate solidification shape for thermal analysis.

According to one embodiment, the sampling device comprises a container adapted to be immersed into a metal melt and filled with a sample quantity of said metal melt. The container comprises a top part open at the top end thereof, a bottom part adapted to be the first part of the container immersed into the melt when taking a sample quantity, and an essentially cylindrical part arranged between the top part and the bottom part. The container further comprises an inner wall member and an outer wall member. The inner wall member has an inner surface intended to contact a sample quantity of the metal melt during thermal analysis, and an outer surface. The outer wall member has an inner surface, and an outer surface adapted to be exposed to the ambient air during thermal analysis. The inner wall member and the outer wall member are essentially coaxially arranged in the cylindrical part of the container and joined at the top part of the container, and the inner and outer wall members define a closed insulating space between the outer surface of the inner wall member and the inner surface of the outer wall member. The sampling device further comprises temperature responsive means adapted to extend into the sample quantity during thermal analysis.

The bottom part of the container is preferably essentially semi-spherical in order to provide the intended simulation of a spherical solidification. The bottom part may also comprise a flattened part arranged at the bottom end of the bottom part and essentially perpendicular to a central axis of the container. The distance between the outer surface of the inner wall member and the inner surface of the outer wall member at the flattened part may suitably be smaller than the distance between the outer surface of the inner wall member and the inner surface of the outer wall member in the cylindrical part of the container. This further improves the heat loss and simulated spherical solidification.

The process of manufacturing a sampling device according to the present invention comprises providing a sampling device comprising a container. A composition as described above is applied to at least a part of an inner surface of the container, said inner part of the surface of the container intended to face a metal melt during thermal analysis. Thereafter the solvent of the composition is dried off or evaporated off such that a dry coating is achieved.

Even though the composition according to the present invention is mainly developed for use in a sampling device for thermal analysis of solidifying metal melts, such as compacted graphite iron and ductile iron, it may also be used for coating of other articles used in connection with the production of metal melts. For example, the composition may be used for coating of ladles, troughs, moulds or any other surface of an article, such as a metal article, adapted to face a metal melt, particularly an iron, aluminium or zinc based melt.

Furthermore, a coating which reduces the content of magnesium in a metal melt in contact with the coating may also be used in other applications, for example in applications where a microstructural modification is desired in the surface of a casting. For example, it may be used for achieving a microstructure at a surface of a cast component different than a microstructure in the centre of the cast component such as for achieving different properties at the surface than in the bulk of the component.

BRIEF DESCRIPTION OF THE DRAWINGS

In the photographs of FIGS. 1a-1e, the distance mark in the lower right corner of each photograph indicates a distance of 100 μm.

DETAILED DESCRIPTION OF THE INVENTION

The invention will be described in more detail below with reference to example embodiments and the accompanying drawings. The invention is not limited to the example embodiments discussed but may be varied within the scope of the appended claims. In the following, "wt-%" means "percent by weight".

The composition may be applied to a surface of an article by any suitable method known in the art, such as painting, dipping, air-spraying or roller-coating.

The composition according to the present invention is particularly suitable for coating of sampling devices used for thermal analysis of solidifying melts, and is especially suitable for coating of sampling devices for thermal analysis of compacted graphite iron and ductile iron.

The composition for coating of a surface intended to be exposed to a metal melt according to the present invention essentially consists of:
 8-18 wt-% of a refractory component;
 50-75 wt-% of solvent, preferably water;
 10-20 wt-% of an inorganic binder;
 0-10 wt-%, preferably 2-10 wt-%, of an organic binder;
 0.3-7 wt-% of pyrite;
 optionally up to 10 wt-% in total, preferably up to 5 wt-% in total, of one or more additional additives; and unavoidable impurities.

The pyrite of the composition constitutes the functional addition which will enable reaction with magnesium in the interface between the coating and the metal melt. Pyrite is an iron sulphide, essentially with the formula $FeS_2$. It is common knowledge that commercial pyrite may comprise impurities and the use of such commercial pyrite may suitably be used in the present invention without departing from the scope thereof. The sulphur in the pyrite will react with dissolved elementary magnesium in the melt thereby reducing the magnesium content available for assisting in the growth of various forms of graphite in a ferrous melt in the vicinity of the surface which has been coated with a coating obtained by means of said composition.

As disclosed in WO 92/06809, the absolute values of the content of dissolved elemental magnesium may vary based on for example other constituents in the melt from which a sample is taken. WO 92/06809 discloses however one specific example wherein up to 0.008% Mg resulted in flaky graphite, 0.008-0.016% Mg resulted in compacted graphite, 0.016-0.30% Mg resulted in a mixture of compacted and nodular graphite, 0.030-0.035% Mg resulted in 80-100% nodular graphite, and more than 0.035% Mg resulted in nodular graphite. Irrespective of the specific conditions in each specific case, the necessary amount of added Mg to an iron based melt in order to achieve the desired microstructure in a casting thereof can be determined by performing thermal analysis of the melt, analysing the result, and adding more Mg to the iron based melt, if necessary, followed by repeated thermal analysis of the iron based melt with the additionally added Mg. Thermal analysis of an iron based melt can be performed as many times as necessary to ensure that the desired microstructure is achieved during subsequent casting of the melt.

It has been found that the sulphur of the coating cannot be added to the composition in any manner. For example, it is not possible to add the sulphur in the form of elemental sulphur since elemental sulphur will burn off when the coating comes into contact with a metal melt, for example during thermal analysis using a sampling device which has been coated with the coating. If the sulphur is burnt off, it will not be available for reaction with the metal melt in contact with the coating. Tests have shown that elemental sulphur in a coating does not result in the desired reduction of elementary magnesium. Therefore, it is essential that the sulphur of the coating is added in the form of pyrite.

The composition comprises at least 0.3 wt-% pyrite, which is necessary in order to get the desired function of a coating obtained by the composition. According to a preferred embodiment, the composition comprises at least 2 wt-% of pyrite to be appropriately active, preferably at least 3 wt-% of pyrite.

Moreover, the composition comprises at most 7 wt-% of pyrite. Higher contents of pyrite may in some cases cause porosity or other damages in a casting obtained in contact with a surface comprising a coating obtained by the composition. Furthermore, higher amounts of pyrite than about 7 wt-% are not expected to give additional benefits in terms of wall reaction and are therefore not necessary. According to a preferred embodiment, the composition comprises up to 6 wt-% pyrite, more preferably up to 5 wt-% pyrite.

The amount of pyrite may in any case be selected based on the metal melt to which a surface coated by said composition should be exposed to. By way of example, if the composition is adapted to be used for producing a coating on a surface which is intended to be exposed to ductile iron, the pyrite content of the composition may suitably be 3-6 wt-%; and if the composition is adapted to be used for producing a coating on a surface which is intended to be exposed to compacted graphite iron melt, the pyrite content of the composition may suitably be 0.3-5 wt-%, preferably 0.3-2 wt-%.

The pyrite is preferably added in the form of a granular powder. The average particle size of such a powder may suitably be 40-70 μm to ensure sufficient properties of the coating. The particle size inter alia ensures that the pyrite may be evenly distributed in the coating.

If the particle size is too small, there is a risk of spontaneous crystallisation in the composition. If the particle size is too large, the pyrite may settle in the composition before the coating process has begun or in some cases even during the coating process, thereby causing uneven distribution.

The composition intended for coating of a surface intended to be exposed to a metal melt further comprises a refractory component. The refractory component is not intended to take part in the magnesium reduction reaction and is therefore selected thereafter. The refractory component should be stable at high temperatures and when in contact with metal melts, such as a ferrous melt. According to one preferred embodiment, the refractory component is boron nitride. Boron nitride is advantageous because it does not react with Mg and the high interfacial tension between boron nitride and ferrous melts leads to reduced intimacy of contact and reduced likelihood of adhesion. Other suitable alternatives to be used as refractory component are zirconia and alumina because they are stable at very high temperatures and will not react with a metal melt in contact therewith. It is also possible to use any combination of boron nitride, zirconia and/or alumina as a refractory component of the composition according to the invention.

The refractory component is present in the composition in an amount of at least 8 wt-%, preferably at least 10 wt-%, in order to provide the desired properties of a coating obtained by means of the composition, such as high temperature stability and protection the coated surface to a metal melt. The composition comprises up to 18 wt-% of the refractory component, preferably up to 16 wt-%, more preferably up to 14 wt-%. Too high contents of the refractory component could in some cases make the composition difficult to apply to a surface to be coated by techniques such as dip coating or painting. Furthermore, too high contents of the refractory component may in some cases result in cracking of a coating during use as a result of considerable thermal expansion of the substrate due to the high temperature, especially in the case of metallic substrates. Moreover, the ratio between the refractory component and the binder(s) regulates the final properties of the coating obtained by the composition, such as the adhesion to the substrate, green toughness and strength.

The refractory component of the composition may suitably have an average particle size of about 2-20 μm, preferably 2-15 μm. Other particle sizes of the refractory component are however also plausible depending on the refractory component selected and the other components of the composition in order to ensure the desired properties of the composition, such as viscosity, risk of sedimentation etc.

The composition further comprises 50-75 wt-% of a solvent, preferably 55-70 wt-%, more preferably 60-68 wt-%. The solvent content inter alia regulates the application properties of the composition, such as thickness, uniformity and porosity, when applying the composition to a substrate to be coated. The solvent may for example be an alcohol or water. Water is preferable from an environmental and handling aspect. However, in some cases, for example when coating of sand moulds, an alcohol is preferable in order not to influence the sand negatively. Furthermore, an alcohol may be faster to dry off whereas water may in some cases require forced air drying at a slightly increased temperature, such as about 35-50° C.

Moreover, the composition comprises an inorganic binder which is compatible with the refractory component. The inorganic binder is present in an amount of 10-20 wt-%, preferably 12-18 wt-%, of the composition and acts as a refractory binder. According to a preferred embodiment, the inorganic binder is a silicate in order to provide good heat stability. A silicate is also preferable from the point of view of providing less risk of cracking of a coating obtained by the composition, in case of substantial thermal expansion of the substrate during use, as it imparts a certain plasticity to such a coating. Preferably, potassium silicate or sodium silicate is used.

Furthermore, the composition may also comprise an organic binder in an amount of up to 10 wt-%, preferably 2-10 wt %, of the composition and is intended to burn off during use of the coating in contact with a melt due to the high temperature. The organic binder is preferably acrylic.

The composition may also comprise one or more additional additives up to 10 wt-% in total. Such additives may for example be selected from the group consisting of surfactants, viscosity modifiers, additives for flowability, additives for high temperature stability and mixtures thereof. For example, graphite may suitably be added in an amount of up to 2 wt-% for improving flowability and high temperature stability of the coating, especially when the composition comprises boron nitride as a refractory component. Moreover, diethylene glycol monobutyl ether may be added in an amount of up to 5 wt-%, preferably 2-4 wt-%, for further improving the adherence of the coating to a metallic surface, such as a steel surface, if desired.

According to one specific embodiment of the present invention, the composition for coating of a surface intended to be exposed to a metal melt essentially consists of:
- 8-18 wt-%, preferably 10-16 wt-%, of boron nitride;
- 50-75 wt-%, preferably 55-70 wt-%, of water;
- 10-20 wt-%, preferably 12-18 wt-% of potassium silicate;
- 2-10 wt-%, preferably 4-8 wt-%, of acrylic;
- 0.3-7 wt-% of pyrite;
- optionally up to 5 wt-% of diethylene glycol monobutyl ether;
- optionally up to 2 wt-% of graphite; and
- unavoidable impurities.

When the composition for coating of a surface intended to be exposed to a metal melt has been applied to a substrate, the solvent of the composition is essentially removed, for example by drying or evaporation. Drying may for example be performed by using forced air drying at a slightly elevated temperature, such as about 35-50° C. An essentially dry coating on a substrate is thus obtained.

The coating according to the invention essentially consists of:
- 26-60 wt-%, preferably 33-55 wt-%, of a refractory component;
- 33-67 wt-%, preferably 40-60 wt-%, of an inorganic binder;
- 0-3.5 wt-%, preferably 1.5-3.5 wt-%, of an organic binder;
- 1-23 wt-% of pyrite;
- optionally up to 10 wt-%, preferably up to 5 wt-%, of residual solvent;
- optionally up to 33 wt-% in total, preferably up to 16 wt-% in total, of one or more additional additives; and
- unavoidable impurities.

The refractory component, inorganic binder, organic binder, solvent and additional additives of the coating, respectively, are the same as has been mentioned in respect of the composition above and will therefore not be explained further. Since the coating is obtained by drying or evaporating the solvent, the particle sizes mentioned above remains the same. Furthermore, there may be residual solvent up to 10 wt-% remaining in the coating after the drying and/or evaporation of solvent. Such residual solvent may be bound to the other components of the coating and the coating is therefore essentially dry.

The coating comprises at least 1 wt-% of pyrite, preferably at least 6.5 wt-% pyrite, and more preferably at least 10 wt-% pyrite. Furthermore, the coating comprises at most 23 wt-% pyrite, preferably at most 20 wt-% pyrite, more preferably at most 16.5 wt-% pyrite.

According to one specific embodiment of the present invention, the coating essentially consists of:
- 26-60 wt-%, preferably 33-55 wt-%, of boron nitride;
- 33-67 wt-%, preferably 40-60 wt-%, of potassium silicate;
- 1.5-3.5 wt-% of acrylic;
- 1-23 wt-% of pyrite;
- optionally up to 10 wt-%, preferably up to 5 wt-%, of residual water;
- optionally up to 16.5 wt-% of diethylene glycol monobutyl ether;
- optionally up to 6.5 wt-% of graphite;
- and unavoidable impurities.

As mentioned above in regard to the composition for coating of a surface intended to be exposed to a metal melt, the amount of pyrite may in any case be selected based on the metal melt to which the coating should be exposed. By way of example, if the coating is adapted to be exposed to a ductile iron melt, the pyrite content of the coating may suitably be 10-20 wt-%; and if the coating is adapted to be exposed to a compacted graphite iron melt, the pyrite content of the coating may suitably be 1-17 wt-%, preferably 1-6.5 wt-%.

As previously mentioned, the composition is especially suitable for coating of sampling devices for thermal analysis of solidifying metal melts.

A sampling device for thermal analysis comprises a container which is intended to be immersed into a melt such that a sample quantity of the melt is allowed to flow into and filling the container. The container, comprising the sample quantity, is then taken out of the melt and thermal analysis is performed. During the thermal analysis, the sample quantity is allowed to solidify and the temperature variation over time is measured using the temperature responsive means. The temperature responsive means is suitably positioned by means of a support member. The support member may advantageously be located above the top end of the container, preferably concentrically with a central axis of the container.

The container generally comprises a top part open at the mouth, i.e. open at the top end thereof, a bottom part adapted to be the first part of the container immersed into the melt when taking a sample quantity of the melt, and an essentially cylindrical part arranged between the top part and the bottom part of the container. Furthermore, the container generally comprises an inner wall member having an inner surface intended to face the sample quantity, and an outer surface opposite the inner surface. The container generally further comprises an outer wall member having an inner surface and an outer surface, wherein the outer surface is adapted to be exposed to the ambient atmosphere during thermal analysis.

The inner and outer wall members may be essentially coaxially arranged at least in the essentially cylindrical part of the container around the central axis of the container. The inner and outer wall members are suitably arranged at a distance from each other except at the top part of the container where they are joined, for example by welding or the like. Thereby, a closed space may be formed between the inner and outer wall members. Thus, such a container is a double-walled container.

The inner and outer wall may suitably each comprise a radially extending flange arranged at the top part of the container, the radially extending flanges of the inner and outer wall being joined together. Thereby, the inner and outer wall members are joined at the top end of the container, i.e. at the mouth thereof. The radially extending flanges of the inner and outer wall members may extend form the respective inner surface of the wall members outwardly in a direction from the central axis of the container such that they will not disturb the filling of the container during sample taking.

The distance between the inner and outer wall members and thus the dimensions of the closed space is an important parameter in regulating the heat loss due to thermal radiation and thermal conduction. By selecting and fully or partly filling the closed space with a suitable medium, and/or altering the dimensions of the space, it is possible to adapt the heat removal rate of the sampling device to the values required for thermal analysis. The closed space may for example be evacuated or filled with gas. It is also plausible to fill the closed space with insulating materials, for example sand or various ceramics, if desired. However, when the closed space is evacuated or filled with gas, such as air, radiation will be an important heat transfer mechanism. As the temperature of the solidifying sample quantity increases, radiation will be of increasing importance since the effect thereof increases with the fourth power of absolute temperature.

The bottom part of the container is preferably semi-spherical in shape. Thus, an angle between a plane perpendicular to the central axis of the container and intersecting the central axis at the very bottom end of the container, and an imaginary line extending from the intersection of said plane and the central axis to the outer surface of the outer wall member at the point where the bottom part and the essentially cylindrical part of the container meet, is about 45°.

Suitably, both the inner wall member and the outer wall member of the container are semi-spherical in the bottom part of the container.

According to one embodiment, the container may further comprise a flattened part in the bottom part thereof. The flattened part is suitably arranged essentially perpendicular to the central axis of the container and has an essentially circular form concentric with the central axis of the container. Thus, an angle between a plane perpendicular to the central axis of the container and intersecting the central axis at the very bottom end of the container, and an imaginary line extending from the intersection of said plane and the central axis to the outer surface of the outer wall member at the point where the bottom part and the essentially cylindrical part of the container meet, is at most about 45°.

Suitably, both the inner wall member and the outer wall member each comprise a flattened bottom portion.

Moreover, the distance between the inner and outer wall members at the flattened part may suitably be smaller than the distance between the inner and outer wall members in the cylindrical part of the container. A sampling device comprising such a flattened bottom and the advantages thereof has for example been disclosed in EP 1 034 419.

The temperature responsive means utilised for thermal analysis of the sample quantity may for example be one or more temperature responsive sensors extending into the sample quantity. Preferably, at least two temperature responsive sensors are used. The first temperature responsive sensor is preferably arranged at the close vicinity of the inner wall member of the container, whereas the second temperature responsive sensor preferably is arranged essentially in the centre of the sample quantity, i.e. essentially in the centre of the container of the sample device. For example, in order to simulate the natural fading of magnesium of an iron-based melt that occurs in both ladle and in castings, the inner surface of the inner wall member, i.e. the surface which is adapted to face and be exposed to the sample quantity during thermal analysis, may be coated with a composition as previously described, thus obtaining the coating also described above. Convection currents generated in the container as a result of the design thereof rinse the sampled iron along the inner surface of the inner wall member of the container and cause a low-magnesium iron to accumulate in the stagnant flow-separated region at the bottom of the container. Thus, the temperature responsive means arranged in the centre evaluates the non-reacted iron, thus determining the start-of-casting behaviour, while the temperature responsive means arranged close to the inner surface of the inner wall member predicts the end-of-casting solidification behaviour.

The temperature responsive sensors are preferably arranged in one or more protective tubes. According to one embodiment, two or more temperature responsive sensors are arranged in one protective tube, which in turn is arranged in the sample device along the central axis of the container and extending into the container such that it will be immersed in the sample quantity during thermal analysis. In such a case, the temperature responsive sensors are arranged inside the protective tube at different locations essentially along the central axis of container. It is however possible to arrange temperature responsive sensor(s) in other manners, for example in different protective tubes and at essentially the same distance parallel to the central axis from the top of the container. Also in this embodiment, a first temperature responsive sensor may suitably be arranged in the close vicinity of the inner surface of the inner wall member whereas a second temperature responsive sensor is arranged essentially in the centre of the sample quantity during thermal analysis.

According to one embodiment, the support member may suitably be attached by legs to the container. The legs enable a sample quantity of a melt to easily flow between the legs into the container when the container is immersed in the melt from which the sample quantity shall be taken, thereby enabling an easy, consistent and reliable process for filling the container with a sample quantity. Moreover, the support member may preferably act as a lid to reduce radiation heat-loss from the top of the sample quantity during thermal analysis. This further aids in the construction of the sample device to simulate a spherical solidification of the sample quantity during thermal analysis, because it balances slower heat loss from the bottom of the container due to the construction thereof.

The inner and outer wall members of the container of the sampling device may for example be made of steel or other suitable material known in the art.

In accordance with the present invention, at least a part of the inner surface of the inner wall member, i.e. the surface which is adapted to face and be exposed to the sample quantity during thermal analysis, is coated with a composition as previously described, thus obtaining the coating also described above.

According to one embodiment, essentially all of the surfaces of the container which may be exposed to a metal melt during taking of a sample for thermal analysis and/or during thermal analysis are coated using the coating composition according to the present invention. Furthermore, other surfaces of the sampling device may also be coated with the composition according to the invention without departing from the scope of the invention.

Other examples of sampling devices which may suitably be coated with the composition according to the present invention includes the sampling devices disclosed in WO 97/35184 and WO 96/23206.

The composition may be used for coating substrates intended to be exposed to a metal melt, such as substrates of sands, ceramics and metals, such as steels. Thus, the composition may also suitably be used for coating of surfaces of for example sand moulds, permanent moulds, ladles, or the like, which surfaces are intended come into contact with a metal melt. In fact, the composition according to the present invention may be used for coating any surface which is intended to be exposed to a metal melt, especially when a coating capable of enabling a reaction with sulphur of a solidifying melt in the vicinity of such a surface is desired.

Experimental Test 1

Sample compositions for coating of surfaces intended to contact a metallic melt were produced by adding different amounts of pyrite to a standard mould coating composition sold under the trade name Teno Zir 6512 by Foseco which comprises zirconia as the refractory component, silicate as the inorganic binder and alcohol as solvent. The amount of added pyrite for the different sample compositions is disclosed in Table 1.

The sample compositions were applied by brushing to a hand moulded sand mould in different cavities of the same mould and dried. An iron based melt comprising about 3.7 wt-% C, 2.2 wt-% Si, 0.3 wt-% Mn and 0.006 wt-% S was cast in the different cavities of the mould. Thereafter, the microstructure at the surface of the castings was investigated by optical microscopy. The resulting depth of the flake skin developed at the surface of the casting for each sample is given in Table 1. A depth of a flake skin is considered to be an average depth where flakes of graphite are detectable.

TABLE 1

Figure 1A:
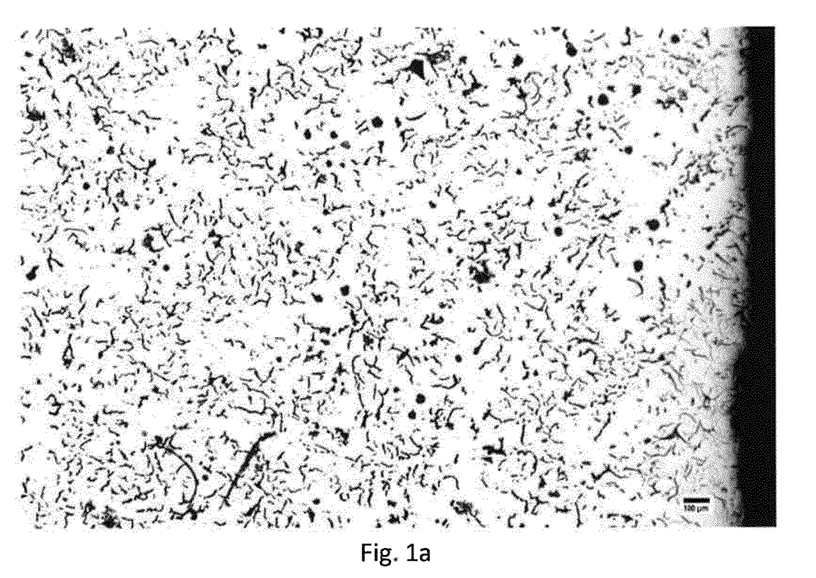
FIG. 1a illustrates a LOM (Light Optical Microscope) photograph of a surface of a casting obtained in contact with a coating obtained by means of a composition free from addition of pyrite.
Figure 1B:
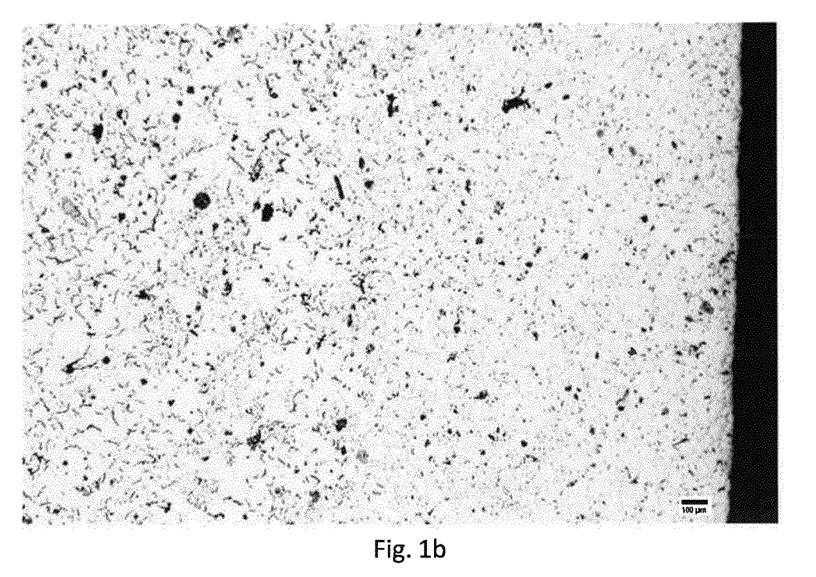
FIG. 1b illustrates a LOM photograph of a surface of a casting obtained in contact with a coating obtained by means of a composition comprising 0.6 wt-% pyrite.
Figure 1C:
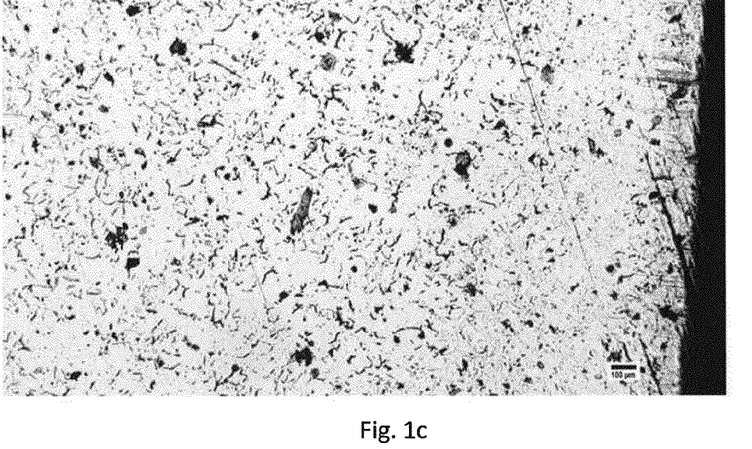
FIG. 1c illustrates a LOM photograph of a surface of a casting obtained in contact with a coating obtained by means of a composition comprising 2 wt-% pyrite.
Figure 1D:
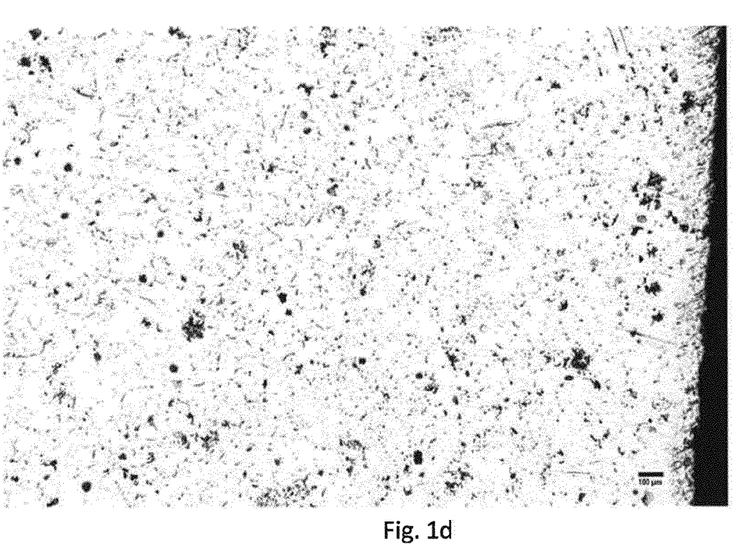
FIG. 1d illustrates a LOM photograph of a surface of a casting obtained in contact with a coating obtained by means of a composition comprising 4 wt-% pyrite.
Figure 1E:
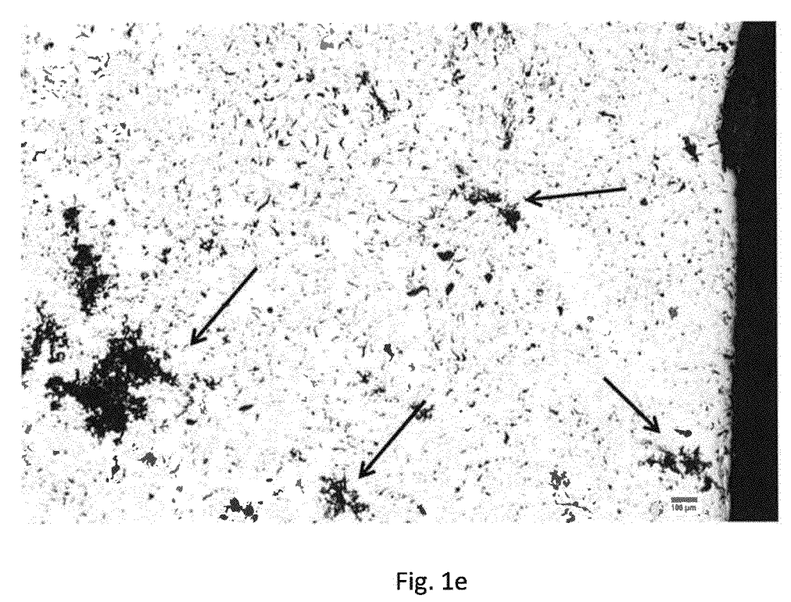
FIG. 1e illustrates a LOM photograph of a surface of a casting obtained in contact with a coating obtained by means of a composition comprising 8 wt-% pyrite.

| Sample | Amount of added pyrite [wt-%] | Depth of flake skin [mm] | Figure |
|---|---|---|---|
| 1.1 | 0 | 0.2 | FIG. 1a |
| 1.2 | 0.60 | 1.3 | FIG. 1b |
| 1.3 | 2 | 1.3 | FIG. 1c |
| 1.4 | 4 | 1.8 | FIG. 1d |
| 1.5 | 8 | 2.7 | FIG. 1e |

As can be seen from the results, a considerably thicker flake skin is achieved for sample compositions comprising a pyrite addition compared to a sample composition where no pyrite has been added (Sample 1.1). Thus, it is clear that an addition of 0.60 wt-% pyrite has an effect on the microstructural changes of the melt during solidification. This is caused by the reaction of sulphur present in the pyrite component of the coating with the Mg of the iron based melt cast in the cavities of the mould.

FIGS. 1a-1e show LOM photographs of the surface microstructure of the castings obtained. As shown, and emphasized by arrows, in FIG. 1e, when a composition of the coating comprising 8 wt-% pyrite was used, large porosities were noted resulting from large areas of shrinkage. These appeared even close to the surface of the casting. Thus, an addition of 8 wt-% of pyrite is clearly disadvantageous.

Even though the experimental test described above was performed in a sand mould, similar results will also be achieved when used on a metallic mould or any other type of metallic substrate surface, such as a sampling device of metallic material coated with the sample compositions given above.

Moreover, it should be noted that even though the experimental test described above utilised a composition which comprises alcohol as the solvent, similar results may be expected also for compositions for coating comprising for example water as the solvent since the solvent of the composition is essentially vaporised before the coating obtained by the composition comes in contact with the metallic melt.

Experimental Test 2

Sample compositions for coating of surfaces intended to contact a metallic melt were produced by adding 2.3 wt-% pyrite to a composition comprising about 12 wt-% of boron nitride as the refractory component, about 74 wt-% of water as a solvent, about 15 wt-% potassium silicate as an inorganic binder, about 5 wt-% of acrylic as an organic binder and about 4 wt-% of additional additives.

Sampling devices, having a configuration as described in EP 1 034 419, were coated with the sample compositions by dip coating followed by drying at about 40° C. using forced air. The coated sampling devices were then used for thermal analysis of ductile iron under full scale production conditions of ductile iron.

A stepping test was conducted wherein a sample was taken when the Mg content of the ductile iron melt was at an initial low content, and the Mg content was increased stepwise six times to the intended final Mg content of the ductile iron melt. Thus, a total of seven different samples were taken. The reason was to determine if the pyrite content of the coating was sufficient to enable determining different contents of Mg.

During thermal analysis, two temperature responsive means were used to record temperature curves during solidification of the sample quantities, one temperature responsive means arranged in the centre of the sample quantities and one arranged in the close vicinity of the inner surface of the container of the sampling device, and the heat released by the reaction was calculated and evaluated in a manner as disclosed for example in U.S. Pat. No. 6,571,856, hereby incorporated by reference.

The result showed that the thermal heat release for the different samples ranged from about 20 J/g for the first sample (lowest Mg content) to about −3.7 J/g for the last sample (highest Mg content).

The range of the measurable thermal heat release is approximately 0-100 J/g and a suitable composition for use for coating of a sampling device for thermal analysis in full scale production of a metal melt should preferably be in the lower part of said range in order to also allow higher values within said range caused by normal variations during full scale production of metal melts.

The experimental test was repeated on another day (the average Mg-content in the sampled ductile iron might thus have been other than in the case above), but with a sample composition where 4 wt-% pyrite was added. The thermal heat release in this case ranged from about 41 J/g to about 12 J/g.

From the test results given above, it is clear that a 4 wt-% pyrite addition is better than a 2.3 wt-% addition since it allows for more variations in full scale production. More specifically, the higher concentration of pyrite allows for measurements of irons that are over-treated with Mg whereas the lower concentration of pyrite is better for measuring iron that is well under-treated with Mg. As the normal practice is to over-treat an iron-based melt with Mg, the higher concentration of pyrite gives yields better resolution during thermal analysis for such a condition. However, both pyrite contents provided acceptable results.

Experimental Test 3

Three sample compositions for coating of surfaces intended to contact a metallic melt were produced by adding different amounts of pyrite to a composition comprising about 12 wt-% of boron nitride as the refractory component, about 74 wt-% of water as a solvent, about 15 wt-% potassium silicate as an inorganic binder, about 5 wt-% of acrylic as an organic binder and about 4 wt-% of additional additives. The amount of added pyrite for the different sample compositions was 3 wt-%, 6 wt-% and 9 wt-%, respectively.

Sampling devices, having a configuration as described in EP 1 034 419, were coated with the sample compositions by dip coating followed by drying at about 40° C. using forced air. The coated sampling devices were used for thermal analysis of ductile iron under full scale production conditions of ductile iron. The experiment was performed in the same ductile iron melt for all three sample compositions.

Thermal analysis was used to determine the thermal heat release in the same way as described in Experimental test 2.

It was found that the thermal heat release for the sample composition comprising 3 wt-% pyrite was about 42 J/g, whereas the thermal heat release for both the sample composition comprising 6 wt-% pyrite and the sample composition comprising 9 wt-% pyrite were about 58 J/g. Thus, it is clear that an increase of pyrite content from 3 wt-% to 6 wt-% increases the heat release and the results thus indicate an increase in the consumption of elementary Mg from the melt with increasing pyrite content, whereas increasing the pyrite content from 6 wt-% to 9 wt-% have no substantial effect. Thus, the pyrite content can suitably be kept lower than 9 wt-% for optimisation of results obtainable during thermal analysis of iron melts with common Mg levels.

The invention claimed is:

1. A composition for coating of a surface intended to be exposed to a metal melt, the composition consisting essentially of:
   8-18 wt-% of a refractory component;
   50-75 wt-% of solvent;
   10-20 wt-% of an inorganic binder;
   0-10 wt %, of an organic binder;
   0.3-7 wt-% of pyrite;
   and optionally up to 10 wt-% in total of one or more additional additives; and unavoidable impurities.

2. The composition according to claim 1, wherein the refractory component is selected from the group consisting of boron nitride, zirconia, alumina and mixtures thereof.

3. The composition according to claim 1, wherein the inorganic binder is a silicate.

4. The composition according to claim 1, wherein the organic binder is acrylic.

5. The composition according to claim 1, wherein the one or more additional additives is/are selected from the group consisting of surfactants, viscosity modifiers, additives for flowability, additives for high temperature stability, additives for improved adhesiveness to a substrate.

6. The composition according to claim 1, wherein a content of pyrite in the composition is 2-6 wt-%.

7. The composition according to claim 1, wherein the pyrite is in the form of a granular powder, with an average particle size of 40-70 μm.

8. The composition according to claim 1, wherein the average particle size of the refractory component is 2-20 μm.

9. A coating consisting essentially of:
   26-60 wt-% of a refractory component;
   33-67 wt-% of an inorganic binder;
   0-3.5 wt % of an organic binder;
   1-23 wt-% of pyrite;
   optionally up to 10 wt % of residual solvent;
   and optionally up to 33 wt-% in total of one or more additional additives; and unavoidable impurities.

10. Coating according to claim 9, wherein the refractory component is selected from the group consisting of boron nitride, zirconia, alumina and mixtures thereof.

11. Coating according to claim 9, wherein the inorganic binder is a silicate.

12. Coating according to claim 9, wherein the organic binder is acrylic.

13. Coating according to claim 9, wherein the one or more additional additives is/are selected from the group consisting of surfactants, viscosity modifiers, additives for flowability, additives for high temperature stability and additives for improved adhesiveness to a substrate.

14. Coating according to claim 9, wherein a content of pyrite in the composition is 6.5-20 wt-%.

15. Coating according to claim 9, wherein the average particle size of pyrite is 40-70 μm.

16. Coating according to claim 10, wherein the average particle size of the refractory is 2-20 μm.

17. An article comprising a substrate, such as a metallic substrate, and a coating according to claim 9.

18. Process for coating of an article, such as a metallic article, comprising applying the composition according to claim 1 to at least a part of the article followed by drying and/or evaporation of the solvent.

19. A sampling device for thermal analysis of solidifying metal, comprising a container adapted to comprise a sample quantity of a metal melt during thermal analysis and temperature responsive means adapted to extend into the sample quantity during thermal analysis, the container comprising an inner surface adapted to face a sample quantity of the melt during thermal analysis, and an outer surface adapted to face the ambient atmosphere during thermal analysis, characterised in that at least a part of the inner surface of the container comprises a coating according to claim 9.

20. Process of manufacturing a sampling device for thermal analysis of solidifying metal, the process comprising providing a sampling device comprising a container adapted to comprise a sample quantity of a metal melt during thermal analysis the container comprising an inner surface adapted to face a sample quantity of the melt during thermal analysis, and an outer surface adapted to face the ambient atmosphere during thermal analysis, characterised in applying a composition according to claim 1 to at least a part of the inner surface of the container and subjecting the composition to a drying and/or evaporation step.

21. Process according to claim 20, wherein applying said composition is performed by painting or brushing the inner surface of the container with the composition or dipping the container into said composition.

22. The composition according to claim 1, wherein the solvent is water.

23. The composition according to claim 1, wherein a content of the organic binder in the composition is 2-10 wt-%.

24. The composition according to claim 3, wherein the silicate is sodium silicate or potassium silicate.

25. The composition according to claim 6, wherein the content of pyrite in the composition is 3-5 wt-%.

26. The coating according to claim 9, wherein a content of the organic binder in the composition is 1.5-3.5 wt-%.

27. The coating according to claim 11, wherein the silicate is sodium silicate or potassium silicate.

28. The coating according to claim 14, wherein the content of pyrite in the composition is 10-16.5 wt-%.

* * * * *